US008712122B2

(12) United States Patent
Syeda-Mahmood et al.

(10) Patent No.: US 8,712,122 B2
(45) Date of Patent: Apr. 29, 2014

(54) SHAPE BASED SIMILARITY OF CONTINUOUS WAVE DOPPLER IMAGES

(75) Inventors: Tanveer F. Syeda-Mahmood, San Jose, CA (US); David James Beymer, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 455 days.

(21) Appl. No.: 13/076,981

(22) Filed: Mar. 31, 2011

(65) Prior Publication Data

US 2012/0250957 A1 Oct. 4, 2012

(51) Int. Cl.
*G06K 9/00* (2006.01)

(52) U.S. Cl.
USPC ........................................................ 382/128

(58) Field of Classification Search
None
See application file for complete search history.

(56) References Cited

U.S. PATENT DOCUMENTS

| | | | |
|---|---|---|---|
| 4,770,184 | A | 9/1988 | Greene, Jr. et al. |
| 5,935,074 | A | 8/1999 | Mo et al. |
| 6,556,860 | B1 | 4/2003 | Groenewegen |
| 6,716,175 | B2 | 4/2004 | Geiser et al. |
| 6,730,035 | B2 | 5/2004 | Stein |
| 6,905,468 | B2 | 6/2005 | McMorrow et al. |
| 7,624,029 | B1 | 11/2009 | Ghouri |
| 7,693,315 | B2 | 4/2010 | Krishnan et al. |
| 7,695,439 | B2 | 4/2010 | Jackson et al. |

FOREIGN PATENT DOCUMENTS

| | | |
|---|---|---|
| WO | 0176461 | 10/2001 |

OTHER PUBLICATIONS

T. Syeda-Mahmood et al., "Characterizing Spatio-temporal PAtterns for Disease Discrimination in Cardiac Echo Videos" medical image computing and computer-assisted Intervention—MICCAI 2007. Lecture notes in computer science vol. 4791, 2007, pp. 261-269.*
Xiang Sean Zhou, Sonja Zillner, Manuel Moeller, Michael Sintek, Yiqiang Zhan, Arun Krishnan, and Alok Gupta. 2008. Semantics and CBIR: a medical imaging perspective. In Proceedings of the 2008 international conference on Content-based image and video retrieval (CIVR '08).*
J. Tschirren et al, "Automated Analysis of Doppler Ultrasound Velocity Flow Diagrams". IEEE Transaction on medical imaging, vol. 20, No. 12, Dec. 2001.*
Barea et al., Automatic Measurement of Blood Flow Using Artificial Vision, IEEE International Conference on Devices, Circuits and Systems, 1998.

(Continued)

*Primary Examiner* — Atiba O Fitzpatrick
*Assistant Examiner* — Thomas A James
(74) *Attorney, Agent, or Firm* — Lieberman & Brandsdorfer, LLC

(57) ABSTRACT

Continuous wave Doppler images in a data base comprising cardiac echo studies are processed to separate Doppler frames. The frames are pre-processed to extract envelope curves and their corner shape features. Shape patterns in Doppler images from echo studies of patients with known cardiac (valvular) diseases are employed to infer the similarity in valvular disease labels for purposes of automated clinical decision support. Specifically, similarity in appearance of Doppler images from the same disease class is modeled as a constrained non-rigid translation transform of velocity envelopes embedded in these images. Shape similarity between two Doppler images is then judged by recovering the alignment transform using a variant of dynamic shape warping. Since different diseases appear as characteristic shape patterns in Doppler images, measuring the similarity in the shape pattern conveyed within the velocity region of two Doppler images can infer the similarity in their diagnosis labels.

18 Claims, 9 Drawing Sheets

(56) References Cited

OTHER PUBLICATIONS

Dy et al., Unsupervised Feature Selection Applied to Content-Based Retrieval of Lung Images, IEEE Transactions on Pattern Analysis and Machine Intelligence, 25(3): 373-378, 2003.
Liu et al., Classification-Driven Medical Image Retrieval, Proceedings of the IU Workshop, 1998.
Magagnin et al., Semi-Automated Analysis of Coronary Flow Doppler Images: Validation with Manual Tracings, Proceedings of the 28th IEEE, EMBC Annual International Conference, 2006.
Muller et al., A Review of Content-Based Image Retrieval Systems in Medical Applications-Clinical Benefits and Future Directions, International Journal of Medical Informatics, 73(1):1-23, 2004.
Otsu, A Threshold Selection Method From Gray-Scale Histogram, IEEE Transactions on Systems, Man, and Cybernetics, 9(1):62-66, 1979.
Shechner et al., Image Analysis of Doppler Echocardiography for Patients with Atrial Fibrillation, International Symposium on Biomedical Imaging, 2004.
Tagare et al., Medical Image Databases: A Content-Based Retrieval Approach, Journal of the American Medical Informatics Association, 4:184-198, 1997.
Tschirren et al., Automated Analysis of Doppler Ultrasound Velocity Flow Diagrams, IEEE Transactions on Medical Imaging, 20(12):1422-1425, 2001.
Gustavsson et al., A Model-Based Procedure for Fully Automated Boundary Detection and 3D Reconstruction from 2D Echocardiograms, IEEE Computers in Cardiology, 209-212, 1994.
Yu-Bo et al., A New Non-Invasive Technology to Evaluate the Turbulent Shear Stress Immediately Downstream the Heart Valve, Chinese Journal of Biomedical Engineering, 22(2), 2003.
Healy et al., An Automated Method for Analysis and Visualization of Laser Doppler Velocimetry Data, Annals of Biomedical Engineering, 25(2), 336-343, 1997.
Beymer et al., Automatic Estimation of Left Ventricular Dysfunction for Echocardiogram Videos, IEEE 2009.
Bosch et al., Developments Towards Real-Time Frame-To-Frame Automatic Contour Detection on Echocardiograms, IEEE 1991.
Greenspan et al., Doppler Echocardiography Flow-Velocity Image Analysis for Patients With Atrial Fibrillation, Ultrasound in Medicine and Biology, 31(8), 1031-1040, 2005.
Khayum et al., Evaluation of the Severity of Mitral Valvular Regurgitation With Doppler Echocardiography Using Proximal Flow Convergence Method, Journal of Computer Science, 5(2), 115-122, 2009.
Shrestha et al., Experience of Newly Constructed Echocardiography-Database With Video Clips and Color Still Images at the Echocardiography Lab of Nepal Medical College Teaching Hospital, Nepal Medical College Journal, 10(3), 180-183, 2008.
Boyd et al., Remote Digital Echocardiography for the Identification of Cardiac Valvular Disease, Medical Technology Symposium, 139-141, 1998.
Roy et al., State-Based Modeling and Object Extraction From Echocardiogram Video, IEEE Transactions on Information Technology in Biomedicine, 12(3), 366-376, 2008.
Pybus, A Perioperative Echocardiographic Reporting and Recording System, 2004.
Bermejo et al., Spatio-Temporal Mapping of Intracardiac Pressure Gradients. A Solution to Euler's Equation From Digital Postprocessing of Color Doppler M-Mode Echocardiograms, Ultrasound in Medicine and Biology, 27(5), 621-630, 2001.

\* cited by examiner

SHAPE BASED SIMILARITY OF CONTINUOUS WAVE DOPPLER IMAGES

BACKGROUND

This invention relates to electronic medical records. More specifically, the invention relates to Doppler images and medical diagnosis using shape-based similarity of such images.

Patient medical records are now being stored in electronic format. These records include structured data, such as vital signs, recorded diagnosis, and unstructured data, such as the doctor's notes, and diagnostic imaging data. In some areas of medicine, doctors routinely use multiple imaging modalities for decision making. These imaging modalities include, but are not limited to, X-ray imaging, ultrasound, and CT imaging. However, the diagnosis methodology of doctors currently is single sample-guided in that only the data from the given patient is used along with their a priori knowledge to make decisions. In reality, most patients have more than one disease whose combined effect on the diagnostic image appearance can be complex.

Flow Doppler imaging is a technique employed to detect cardiac abnormalities, including but not limited to, heart valve diseases. A continuous wave (CW) Doppler is a type of scan during an ultrasound recording where the shape of the Doppler signal tracings convey information about the functioning of various valves and arterial structures. Traditionally, clinicians have manually traced velocity envelopes to extract measurements such as decay time, pressure gradient, pressure half-time, and velocity time integral, all of which are then matched to normal and abnormal values based on clinical guidelines. While physicians can 'eyeball' certain patterns such as the characteristic M-shape pattern for mitral stenosis, detailed correlation of various patterns to diseases is still not well-documented, let alone be used in automatic identification of such patterns.

BRIEF SUMMARY

This invention comprises a method, system, and article for evaluation of Doppler images and derivation of disease identification information from processing the Doppler images.

In one aspect of the invention, a method is provided for matching a query image with one or more stored images. At least one continuous wave (CW) Doppler image is stored in a database, and a processor extracts an envelope curve from the image. The envelope curve possesses at least one feature associated with the CW image, which is also stored in the database. A processor gathers a query Doppler image, and extracts an envelope curve from a velocity profile of the query image. The processor matches at least one feature associated with the stored envelope curve with at least one feature pertaining to the envelope curve as extracted from the query image. At least one image is retrieved from the database with features matching the features associated with the query image.

In another aspect of the invention, a computer system is provided with a database and a processor. The database stores at least one continuous wave (CW) Doppler image and at least one feature associated with an envelope curve extracted from the CW image. A query manager is provided to gather a query Doppler image and to extract an envelope curve from a velocity profile associated with the query image. An image manager is provided to match at least one of the features associated with the stored image with at least one feature associated with the envelope curve as extracted from the query image by the query manager. Based upon the match, a retrieval manager in communication with the image manager retrieves at least one image from the database with features matching a feature associated with the query image.

In yet another aspect of the invention, a computer program product is provided with a computer readable storage medium having embodied computer readable program code. More specifically, computer readable program code is provided with instructions to store at least one continuous wave (CW) Doppler image in a database, and to store at least one feature from the envelope curve associated with the stored Doppler image. Instructions are also provided to gather a query Doppler image and to extract an envelope curve from a velocity profile associated with the query image. In addition, instructions are provided to match one of the features of the stored image with at least one of the features associated with the envelope curve as extracted from the query image.

Other features and advantages of this invention will become apparent from the following detailed description of the presently preferred embodiment of the invention, taken in conjunction with the accompanying drawings.

BRIEF DESCRIPTION OF THE SEVERAL VIEWS OF THE DRAWINGS

The drawings referenced herein form a part of the specification. Features shown in the drawings are meant as illustrative of only some embodiments of the invention, and not of all embodiments of the invention unless otherwise explicitly indicated. Implications to the contrary are otherwise not to be made.

DETAILED DESCRIPTION

Figure 1:
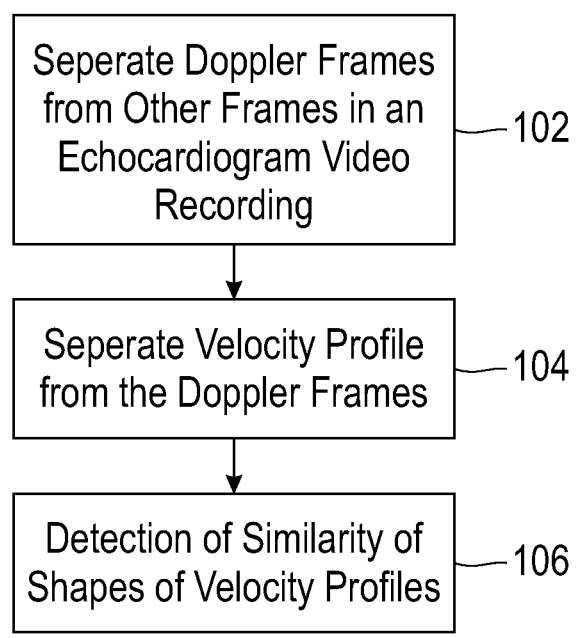
FIG. 1 is a flow chart illustrating a general process for disease recognition and retrieval from Doppler images.

It will be readily understood that the components of the present invention, as generally described and illustrated in the Figures herein, may be arranged and designed in a wide variety of different configurations. Thus, the following detailed description of the embodiments of the apparatus, system, and method of the present invention, as presented in the Figures, is not intended to limit the scope of the invention, as claimed, but is merely representative of selected embodiments of the invention.

The functional units described in this specification have been labeled as managers. A functional unit may be implemented in programmable hardware devices such as field programmable gate arrays, programmable array logic, programmable logic devices, or the like. The functional unit may also be implemented in software for processing by various types of processors. An identified functional unit of executable code may, for instance, comprise one or more physical or logical blocks of computer instructions which may, for instance, be organized as an object, procedure, function, or other construct. Nevertheless, the executables of an identified functional unit need not be physically located together, but may comprise disparate instructions stored in different locations which, when joined logically together, comprise the functional unit and achieve the stated purpose of the functional unit.

Indeed, a functional unit of executable code could be a single instruction, or many instructions, and may even be distributed over several different code segments, among different applications, and across several memory devices. Similarly, operational data may be identified and illustrated herein within the functional unit, and may be embodied in any suitable form and organized within any suitable type of data structure. The operational data may be collected as a single data set, or may be distributed over different locations including over different storage devices, and may exist, at least partially, as electronic signals on a system or network.

Reference throughout this specification to "a select embodiment," "one embodiment," or "an embodiment" means that a particular feature, structure, or characteristic described in connection with the embodiment is included in at least one embodiment of the present invention. Thus, appearances of the phrases "a select embodiment," "in one embodiment," or "in an embodiment" in various places throughout this specification are not necessarily referring to the same embodiment.

Furthermore, the described features, structures, or characteristics may be combined in any suitable manner in one or more embodiments. In the following description, numerous specific details are provided, such as examples of managers, including but not limited to a query manager, an image manager, and a retrieval manager, to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of devices, systems, and processes that are consistent with the invention as claimed herein.

In Doppler imaging, ultrasound waves of a known frequency are transmitted, and the amplitude and frequency of the received signal is recorded. Use of continuous wave (CW) Doppler has become popular for imaging due to its high temporal and velocity resolution. More specifically, with respect to cardiac studies, in the CW scan a shape of signal tracings convey information about functions of various valves and arterial structures. Motion of blood and tissue within the patient induces frequency shifts between transmitted and received signals. With respect to cardiac testing and evaluation, blood moves at a higher velocity than heart tissue, and induces higher frequency shifts than tissue. Accordingly, high-pass filtering of the received signal eliminates a response from the surrounding tissue and provides information exclusively of blood flow.

FIG. 1 is a flow chart (100) illustrating a general process for disease recognition and retrieval from Doppler images. The process is automated for employing CW Doppler images to discover similarities with previously stored images. More specifically, different valvular diseases appear as characteristic shape patterns in CW images. By measuring the similarity in the shape pattern conveyed within a velocity region of two CW images, the similarity of their diagnosis labels can be inferred. Initially, pre-processing of a current CW image is performed to separate Doppler frames from other frames in an echocardiogram video recording (102). Following the pre-processing step, a relevant region of Doppler frames containing velocity profiles is separated and isolated from the Doppler frames in the recording (104). Details of the separation technique is illustrated and explained in detail with reference to FIG. 2. Following the separation and isolation at step (104), the detection of similarity of shapes of velocity profiles is employed to account for variations in heart rate and signal intensity (106). The similarity measures should be robust to individual inter-patient variations in the shape profile within the same disease class, while still being able to discriminate between mild, moderate, and severe cases of disease.

Figure 2:
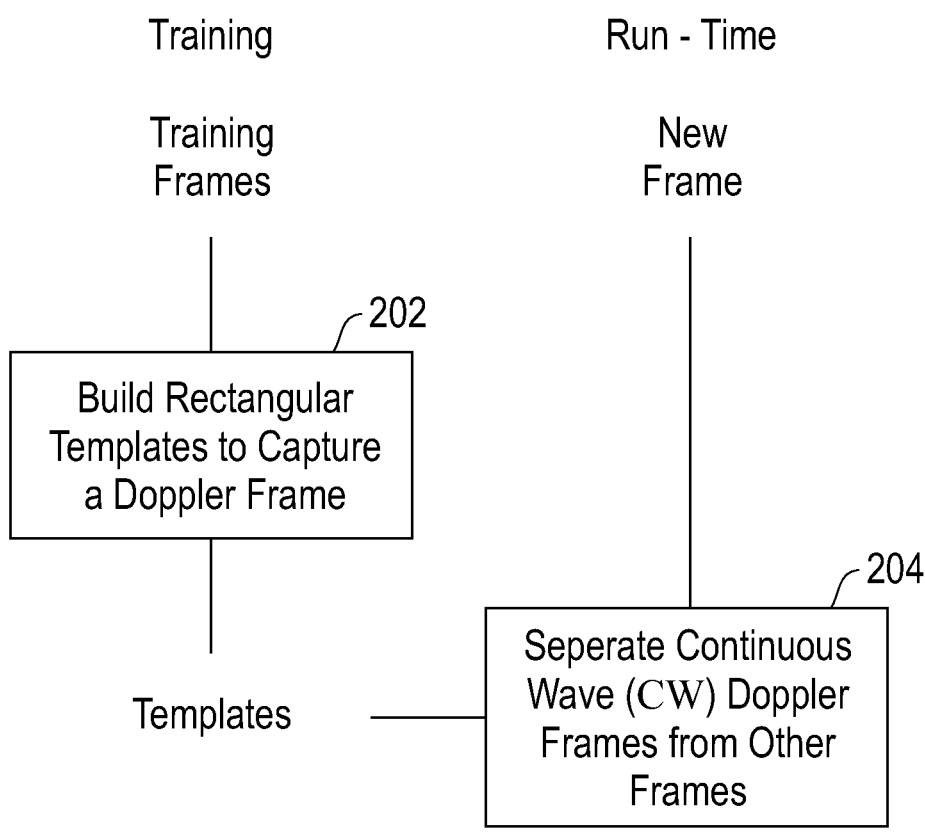
FIG. 2 is a flow chart illustrating the pre-processing step shown in FIG. 1.

As noted above, the pre-processing step separates Doppler frames from other frames in an echocardiogram video, which depicts moving heart regions and textual measurement-only frames. FIG. 2 is a flow chart (200) illustrating details of the pre-processing step. To isolate the Doppler frame, rectangular templates are built to capture the Doppler region through a training process using echo frames from echo machines that capture the position and size of the Doppler regions in an echo video frame (202). By applying the templates at step (204), all Doppler frames in an echo video are isolated. In another embodiment, template correlation is replaced with an optical character recognition (OCR) engine. After applying OCR, the system searches for keywords applied to different Doppler images, such as CW for continuous wave, and PW for pulsed wave, etc.

Figure 3:
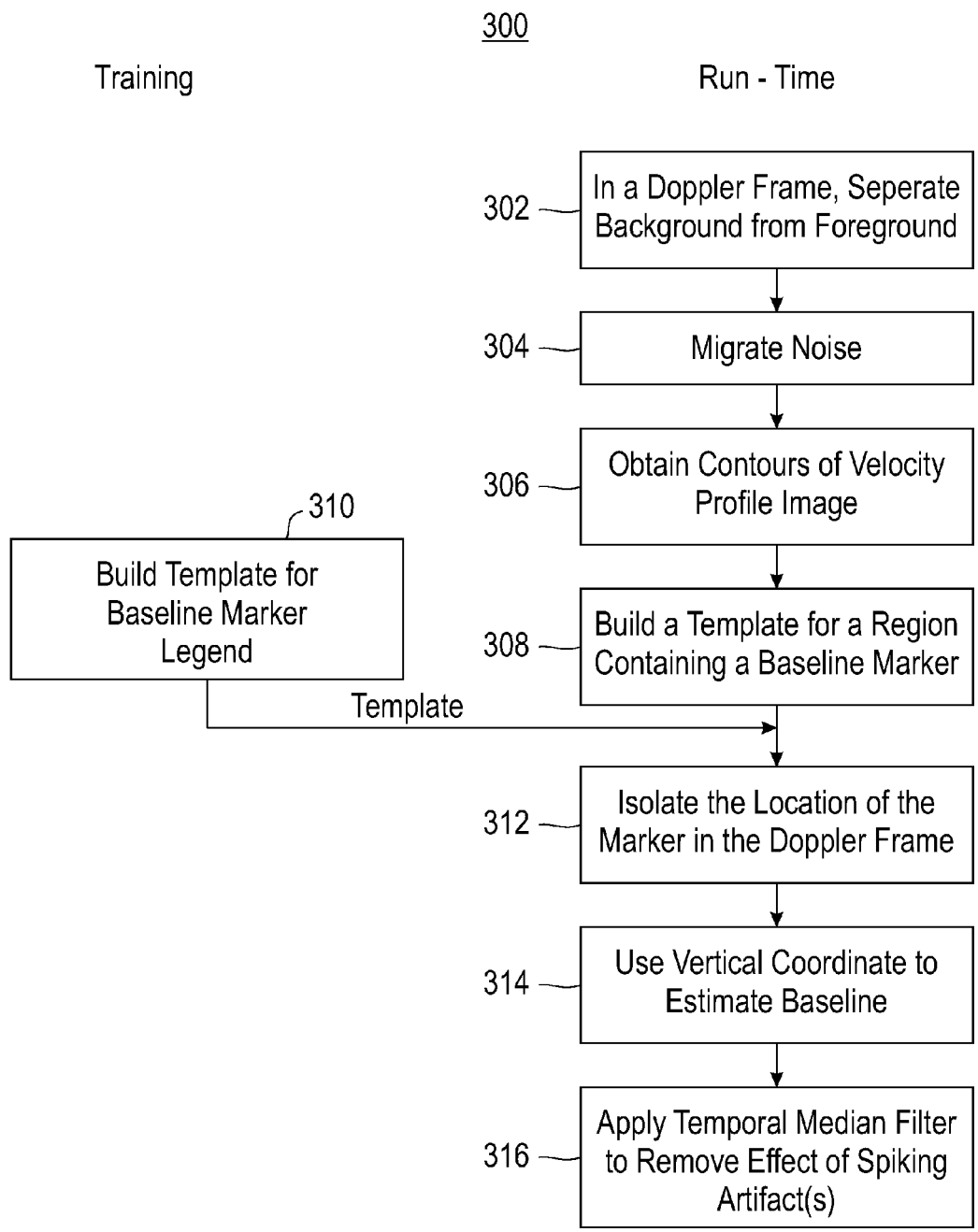
FIG. 3 is a flow chart illustrating the velocity envelope extraction process.

Following completion of the pre-processing, as shown in FIG. 2, velocity envelopes are extracted from the separated Doppler frames to highlight the velocity profiles within a selected region. FIG. 3 is a flow chart (300) illustrating details of the velocity envelope extraction process. Initially, a foreground separation technique is applied to separate the foreground from a background thresholding algorithm (302). In one embodiment, the background thresholding algorithm calculates an optimum threshold separating the foreground and background so that their combined intra-class variance is minimal using a shape of a histogram of pixel intensities. It is known that the thresholding algorithm leaves noise in the resulting images. To resolve noise remnant(s), a morphological close step is applied to mitigate the noise (304). In one embodiment, the close step fills in small holes in image bright regions to yield a clean velocity signal containing region. Following step (304), the boundary pixels of white regions are traced in order to obtain contours of the velocity profile image (306). To extract the final velocity envelope, strong boundaries that are on either side of the baseline, i.e. the horizontal axis, are retained (308). In one embodiment, the baseline can be occluded by measurement bars, measurement screens, or artifacts, and as such, simple image processing may not be sufficient to detect the baseline. To determine the baseline, or origin of velocity, a velocity marker commonly present at the base line is employed. More specifically, a template for the baseline marker legend is built (310), and template matching is employed to isolate the location of the marker in the Doppler frame (312). The vertical coordinate of this region is then used as an estimate of the baseline (314). To remove the effect of spiking artifacts that may be embedded within the velocity signal, a temporal median filter is applied on the extracted envelopes (316).

Figure 4:
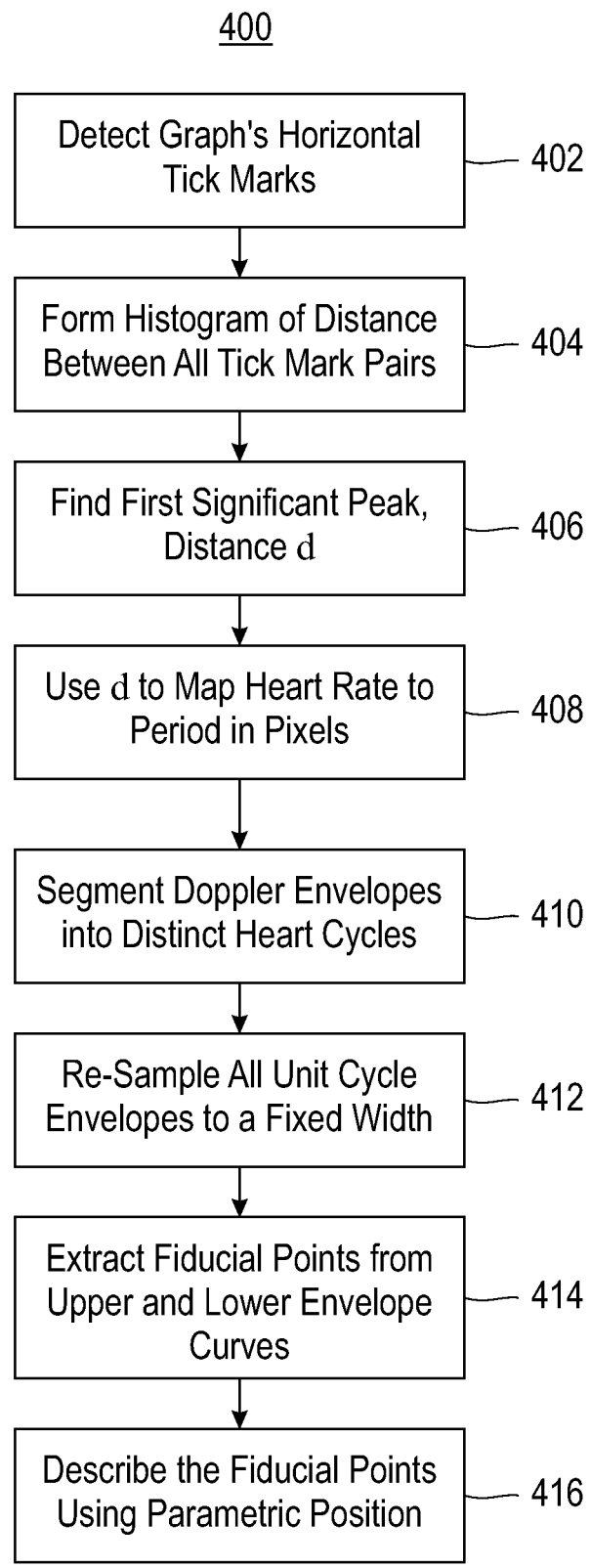
FIG. 4 is a flow chart illustrating the segmenting process.

To make subsequent matching of images invariant to heart rate, the velocity envelopes are segmented into individual heart beat cycles. FIG. 4 is a flow chart (400) illustrating the segmenting process. An estimate of heart rate is obtained from measurement supplied by the echo machine overlayed on the echo frame. In one embodiment, the heart rate is present on the image as embedded text. Template matching may be employed to isolate the indicia and to extract the heart rate in beats per minute. To convert the heart rate from beats per minute to actual pixel widths in the Doppler region, calibration markers are detected on one of the horizontal axis of the Doppler region (402). In one embodiment, the calibration markers are present on a top horizontal axis. Similarly, in one embodiment there is a uniformity associated with spacing of calibration markings. For example, in one embodiment it is known that inter-marking spacing is always 200 ms. With this uniformity, the inter-marking distance, d, may be estimated in pixels to support transformation of time to pixel width. Template matching is employed to detect the calibration markers and to form a histogram of the difference in horizontal coordinates between all pairs of detections (404). In one embodiment, the histogram is dominated by the distance in pixels, d, and integer multiples of d. The first significant peak, distance d, is ascertained (406), and used to map the heart rate to a period in pixels (408). Accordingly, the histogram is processed to ascertain the first significant peak.

Following step (408), the velocity signal region contained within the Doppler velocity envelope is used directly for autocorrelation-based periodicity estimation. More specifically, the Doppler envelopes are segmented into distinct heart cycles using the pixel width information (410). To normalize for intensity and heart rate differences, all unit cycle envelopes are re-sampled to a fixed sample width (412). In one embodiment, to avoid aliasing, the sample width should be larger than the longest time period that can be found in these images. After the velocity envelopes are extracted and a periodicity within each of the velocity envelope curves is determined, fiducial points are extracted from upper and lower envelope curves to numerically describe the envelope curves (414). Envelope curves are pairs for the upper and lower envelopes of the Doppler profile. In one embodiment, the extraction of the fiducial points is in the form of a simple line segment approximation of the envelope curves achieved through a recursive partitioning of the curve, control points on a spline approximation, etc. The extracted fiducial points are chosen as corners in the line segment approximation where the curvature changes significantly. In one embodiment the curvature change associated with a fiducial point ranges from 2 degrees to 178 degrees. Each of the chosen corners is described using its parametric position (416). In one embodiment, the parametric position includes characteristics in the form of an angle and orientation of an angle bisector. Using the angle of the corner ensures that the sharpness of the envelopes is retained as a feature.

Following the processes outlined in FIGS. 1-4, a process for matching Doppler envelopes is employed. The goal of matching Doppler images is to recognize the inherent shape pattern characterizing disease by modeling the overall perceptual similarity in appearance within members of the same disease class. Such a matching should not only be invariant to heart rate, signal intensity, imaging artifacts, but also patient specific details that cause the onset of different events within a heart cycle to shift in time in a non-rigid fashion. Due to period estimation offset errors, the signals may have to be circularly shifted by a fixed translation for a rough alignment before the fine non-rigid alignment described above. Even though the individual velocity envelopes have been segmented into single heart cycles, as shown in FIG. 4, the start of the cycles are not necessarily synchronized. Accordingly, the envelopes have to be circularly rotated to be brought into correspondence prior to matching.

Figure 5:
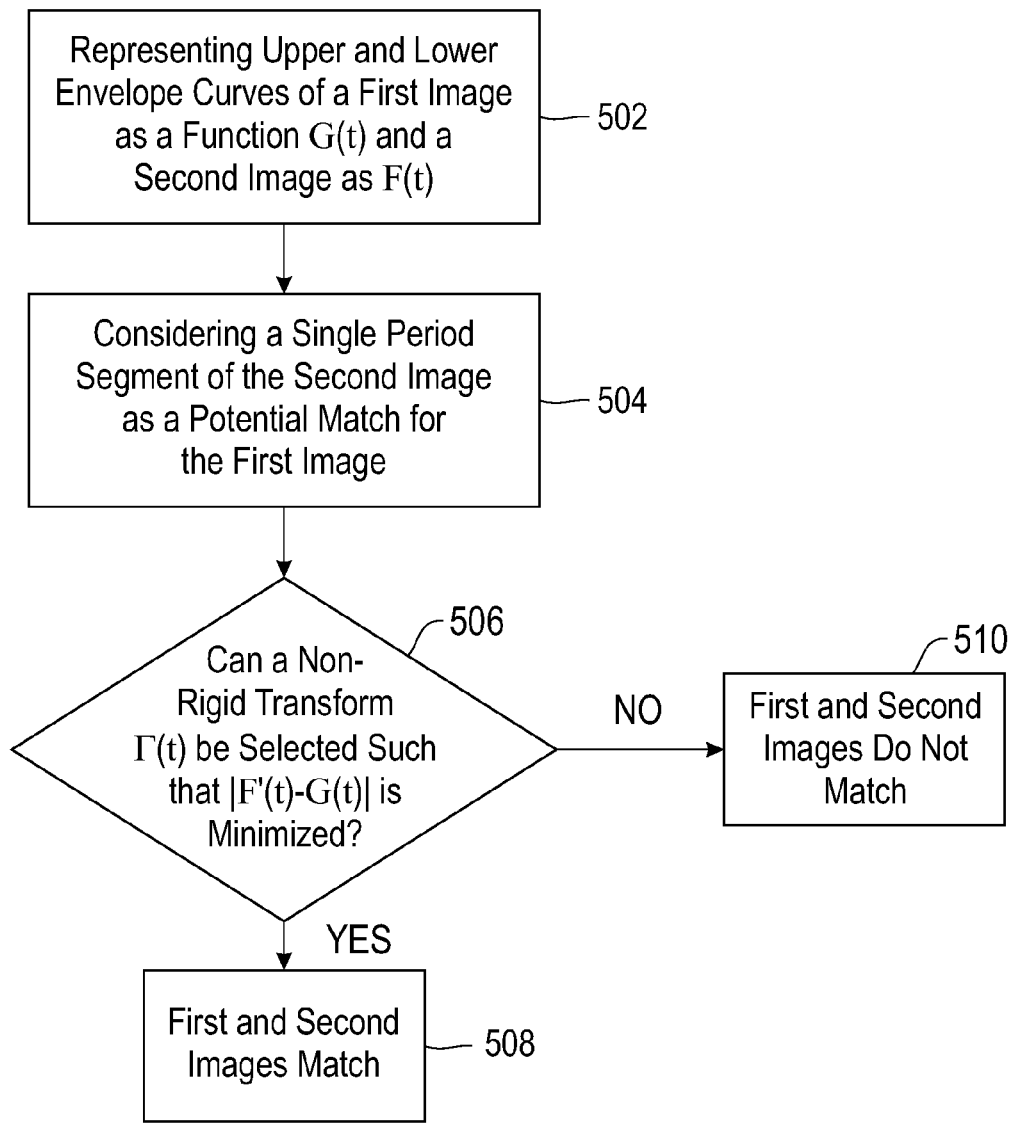
FIG. 5 is a flow chart illustrating the process of matching Doppler images.

At such time as a candidate envelope is determined to be a matching envelope, an identifier correlation can recover the time shift. In one embodiment, the rotation of the signal must be circular in order to preserve the shape. FIG. 5 is a flow chart (500) illustrating the process of matching Doppler images. Assuming that the above-described rotation has taken place, an intra-class shape variation is modeled in a manner that maintains the overall similarity in perceptual appearance as a constrained non-rigid translation transform of the parametric representation of the envelope curves. In one embodiment, two velocity envelopes may be matched based on modeling variations of the envelopes through a constrained non-rigid translation transform that takes into account non-periodic heart beat, variations due to recording level, and differences in the systolic and diastolic phases across patients. The net effect due to these factors defines a non-linear deformation along the time axis.

As illustrated herein, a corresponding alignment transform, $\Gamma$, is retrieved using a shape-based dynamic time warping algorithm that is directed to measuring similarity between two sequences which may vary in time or speed. In step (502), upper and lower envelope curves of a first single period Doppler image segment are represented by a function $G(t)$. In one embodiment, the function is defined as $G(t)=<gl(t); gh(t)>$, where $gl(t)$ and $gh(t)$ define the lower and upper portion of the first velocity envelope curve, respectively. A single period segment of a second Doppler image corresponding to the same disease is considered as a potential match to the first image (504). In one embodiment, a second image segment is represented by a function $F(t)$ defined as $F(t)=<fl(t); fh(t)>$, where $fl(t)$ and $fh(t)$ define the lower and upper portion of a second velocity envelope curve, respectively. A non-rigid transform characterized by $[a, b, \Gamma]$ is applied to the second velocity envelope representation, where $[a, b, \Gamma]$ and can be found such that $|F'(t)-G(t)|<\delta$, where the difference $|F'(t)-G(t)|$ represents a distance metric measuring a difference between $F(t)$ and $G(t)$. In one embodiment, the distance metric is the Euclidean norm and $F'(t)=aF(\Phi(t))$ with $\Phi(t)=bt+\Gamma(t)$, where t is time, bt is a linear component of the transform, and $\Gamma(t)$ is a non-linear translation component. The parameters a and b can be recovered by normalizing in amplitude $F(t)$ and $G(t)$. Since the non-linear translation $\Gamma(t)$ is a function of t, $\Gamma(t)$ can be recovered at important fiducial points (features) in the normalized velocity envelopes. Regarding the velocity envelope as a curve, fiducial points are chosen as the curvature change points or corners in the envelope curves. Accordingly, two velocity envelopes are considered similar if a sufficient quantity of fiducial points between query and target velocity envelopes can be matched using the shape-based dynamic time warping.

Following step (504), an overall shape approximation for the translation $\Gamma(t)$ is recovered by time interpolation. A test is conducted in step (506) to determine whether translation $\Gamma(t)$ can be selected for the velocity envelope representation, $G(t)$, such that it minimizes the approximation error $|F'(t)-G(t)|$ while maximizing the size of a set consisting of matching fiducial points for $F(t)$ and $G(t)$. A positive response to the determination at step (506) is an indication that the first and second Doppler images are considered to be matching (508).

Conversely, a negative response to the determination at step (506) results in a conclusion that the first and second Doppler images do not match (510).

Figure 6:
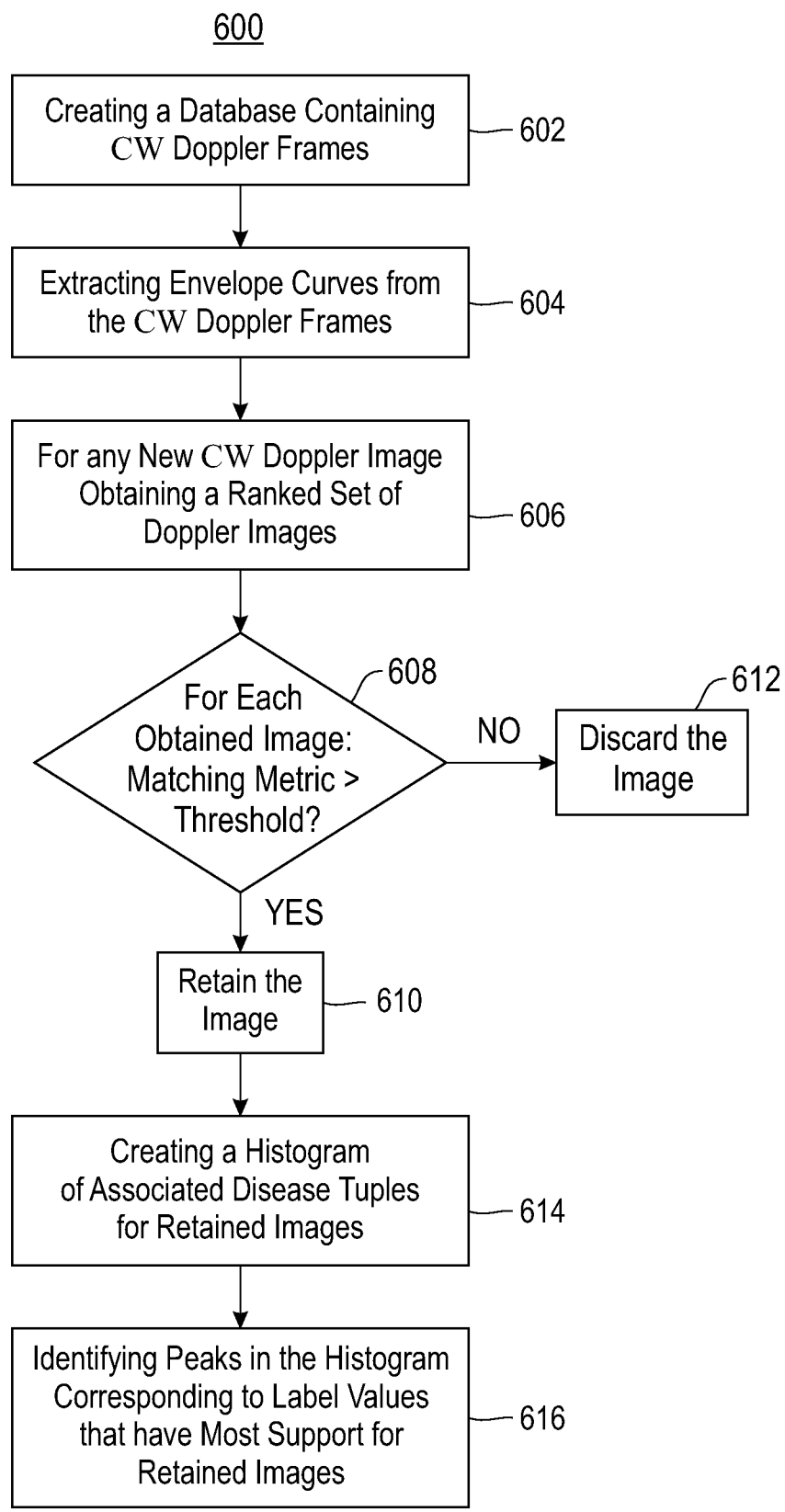
FIG. 6 is a flowchart illustrating a shape-based similarity search algorithm.

Following selection of two matching images, the similarity of the shapes of the images is processed. FIG. 6 is a flowchart illustrating a shape-based similarity search algorithm. As noted above, a database of stored images is created and maintained. During the database creation stage, step (602), all cardiac echo studies are processed to separate Doppler frames. The frames are pre-processed to extract envelope curves and their corner shape features (604). Given any new query Doppler image, a ranked set of matching Doppler images is obtained (606). For each of the retrieved images, it is determined whether the matching metric associated with a retrieved image exceeds a predefined threshold (608). A positive response to the determination in step (608) is followed by retention of the image (610). Alternatively, a negative response is following by discarding the image (612). In one embodiment, a disease class is represented as a 3 tuple (disease type, valve type, severity level). From the set of Doppler images retrieved at step (610), a histogram of their associated disease tuples, including disease type, valve type, and severity type, is separately constructed (614). The peaks in the histogram corresponding to label values that have the most support from the matching images are identified (616). In one embodiment, the identified label values at step (616) have a high probability of being correct values for the query image. Similarly, in one embodiment, statistical distributions are found for other information associated with the patients, such as medications and outcomes for further enhanced decision support.

Figure 7:
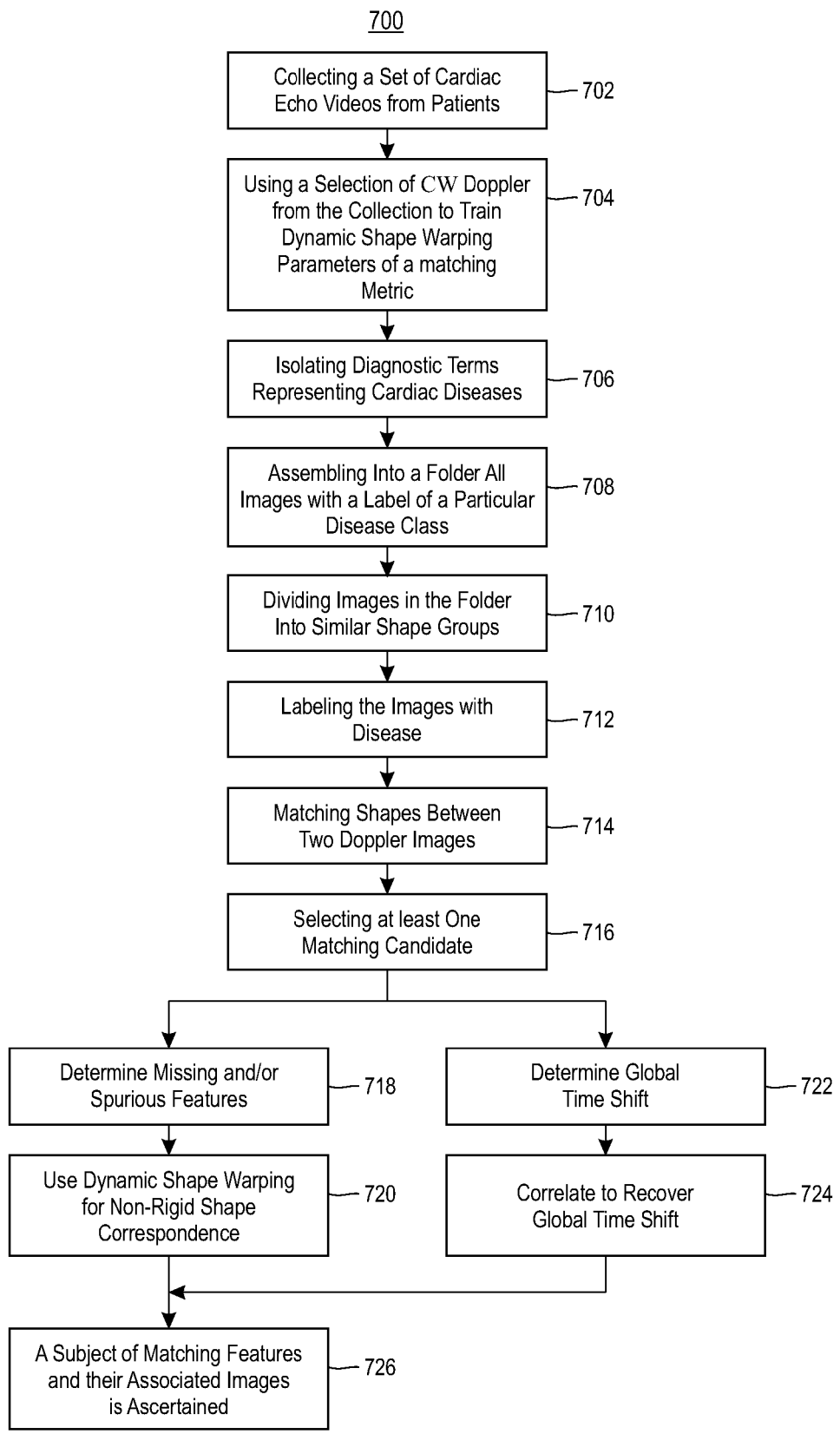
FIG. 7 is a flow chart illustrating application of the processes of FIGS. 1-6.

FIG. 7 is a flow chart (700) illustrating application of the processes of FIGS. 1-6. A set of cardiac echo videos is collected from cardiac patients (702). A selection of CW Doppler frames from the collection is used to train the dynamic shape warping parameters of the matching metric (704). Diagnostic terms corresponding to codes representing a plurality of cardiac diseases are automatically isolated from the reports using text identification techniques (706). All Doppler images from patients with a report label of a particular disease class, e.g. moderate mitral stenosis, is assembled into a folder (708). The images in the folder are divided into similar shape groups by browsing the collection (710). In one embodiment, a few representative images from each shape group are examined to identify the valve as well as the disease state of the valve based on the measurements extracted from the valve. The images are then labeled with the disease, e.g. regurgitation versus stenosis, valve, e.g. mitral, aortic, and severity, e.g. moderate, severe, etc., (712).

Shape matching between two Doppler envelopes, as described above in FIG. 5, is performed (714), including isolating a single heart beat and amplitude normalization. Based upon the actions at step (714), at least one candidate image is selected (716). If it is determined (718) that there are both missing features and/or spurious features, dynamic shape warping is used for non-rigid shape correspondence (720). Similarly, if it is determined that there is a global time shift (722), correlation is used to recover the global time shift (724). Following step (720) or step (724), a subset of matching features and their associated images is ascertained (726). In one embodiment, fiducial point similarity is determined through non-rigid warping. Similarly, in one embodiment, based upon the subset returned at step (726), measurements of precision and recall may be employed to ascertain the accuracy of the shape based matching. Accordingly, the process shown herein supports shaped based matching of CW Doppler images for clinical decision.

Figure 8:
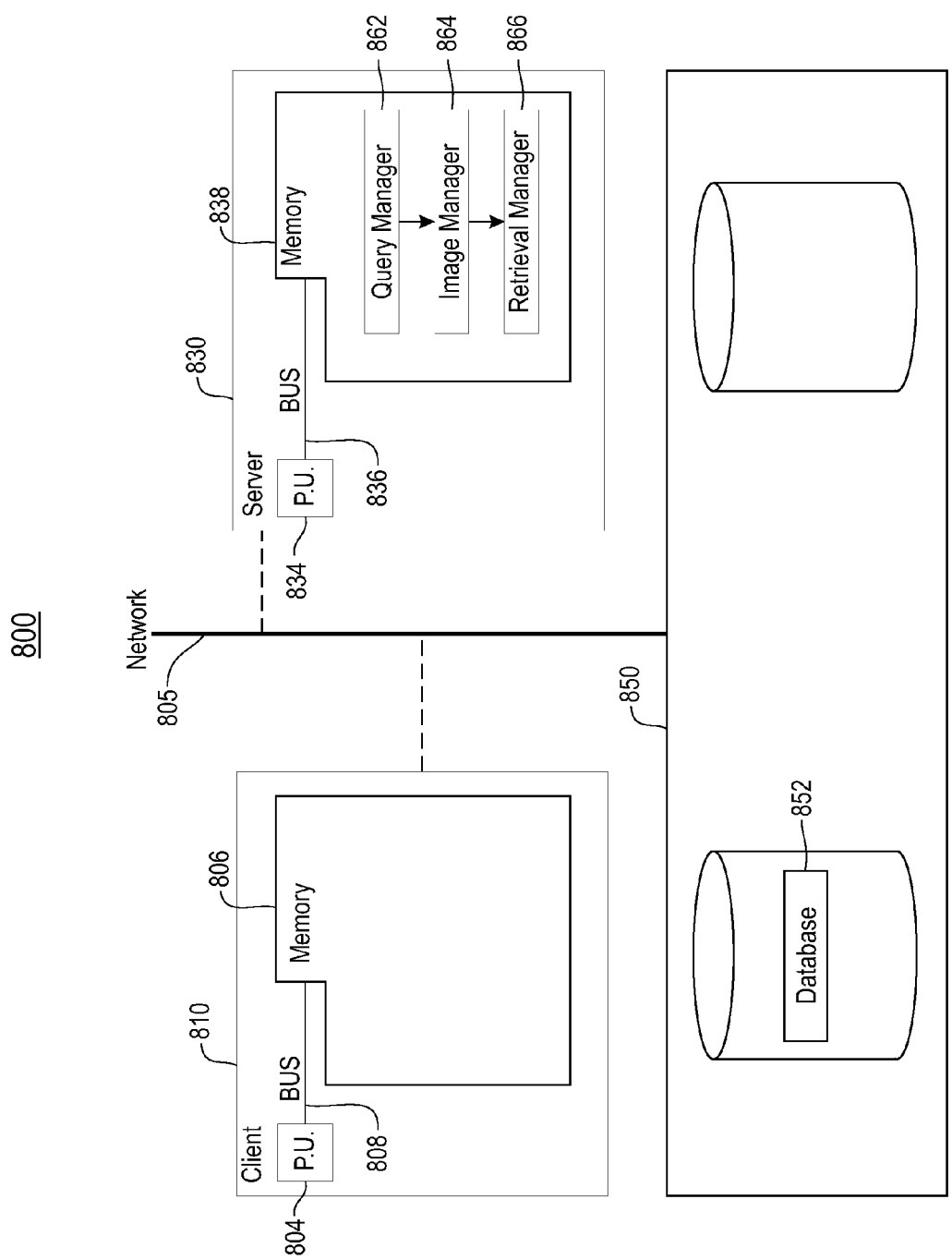
FIG. 8 is a block diagram illustrating tools embedded in a computer system to support image evaluation and disease identification.

As demonstrated in the flow charts of FIGS. 1-7, method are employed to evaluate Doppler images and derive disease identification from image processing. FIG. 8 is a block diagram (800) illustrating tools embedded in a computer system to support image evaluation and disease identification. A computer system is shown with a client machine (810) in communication with a server (830) across a network (805). The client machine (810) is provided with a processing unit (804), in communication with memory (806) across a bus (808) and in communication with data storage (850). Similarly, the server (830) is provided with a processing unit (834), in communication with memory (836) across a bus (838) and in communication with data storage (850). Both the client machine (810) and the server (830) may communicate with data storage (850) across a network connection (805).

As shown herein, the data storage (850) is shown housing a database (852). In one embodiment, the database is employed to store one or more continuous wave (CW) Doppler images and to store at least one feature associated with each stored Doppler image. More specifically, the database is a structure to store and organize both the images and data associated with the images. In addition to the database, tools are provided to support searches of the database for retrieval of similar Doppler images, and to leverage the search results to provide clinical decision support. A query manager (862) is provided local the server (830) and configured to gather a query Doppler image and to test data from the Doppler images being evaluated. To facilitate identification of a disease associated with the Doppler image(s), the query manager processes the image(s) to extract test data from the image(s). In one embodiment, the extracted data includes both an envelope curve and a velocity profile from each image.

The server (830) is provided with an image manager (864) in communication with the query manager (862). The image manager (864) functions to match data from the query image with data stored in the database (852). More specifically, the image manager (864) functions to match one or more features associated with the stored image(s) with one or more features associated with the envelope curve extracted from the query image by the query manager (862). To support communication of the feature match, a retrieval manager (866) is provided in communication with the query manager (862). More specifically, the retrieval manager (866) functions to retrieve from the database at least one image that has characteristics that match the characteristic associated with the query image. Accordingly, the query manager (862), image manager (864), and retrieval manager (866) function to process a query based upon image data.

As discussed above, the query manager (862) is responsible for extraction of specified data from a query image. More specifically, with respect to an echo-cardiogram, the query manager (862) extracts the Doppler image from an echo-cardiogram video, and isolates the velocity profile from the extracted Doppler image. In addition, the query manager (862) functions to determine a heart beat cycle within the identified envelope curve of the query image, and to normalize the envelope curve to include at least one heart beat cycle and a fixed image size.

Furthermore, as noted above, the image manager (864) functions to match a characteristic of the stored image with a characteristic of the envelope curve extracted from the query image. Each characteristic that is associated with the envelope curve reflects a shape of the curve. The match function of the image manager (864) is based upon a shape similarity of the envelope curve of the query image and an envelope curve of one or more stored images. In one embodiment, the image manager (864) selects a non-rigid transform to minimize a difference between the shapes of the envelope curves of the query and stored images. More specifically, the image manager (864) represents one or more of the characteristics of the envelope curves of both the query and stored images through fiducial points. In one embodiment, the fiducial points are selected as corners in a line segment approximation for each envelope curve. Accordingly, the image manager (864) functions to support the backbone of image match and selection.

As identified above, the query managers (862), image manager (864), and retrieval manager (866) function to manage image selection and match for disease identification. The managers are shown residing in memory local to the server. More specifically, query manager (862), image manager (864), and retrieval manager (866) each reside in memory (836) of server (830). In one embodiment, the query manager (862), image manager (864), and retrieval manager (866) may reside as hardware tools external to memory (836) of server (830), or they may be implemented as a combination of hardware and software. Similarly, in one embodiment, the managers and client may be combined into a single functional item that incorporates the functionality of the separate items. As shown herein, each of the managers is shown local to the respective server (830). However, in one embodiment the managers may be collectively or individually distributed across the network and function as a unit to manage image selection to support disease identification. Accordingly, the managers may be implemented as software tools, hardware tools, or a combination of software and hardware tools, to collect and organize data content.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++, Matlab or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 9:
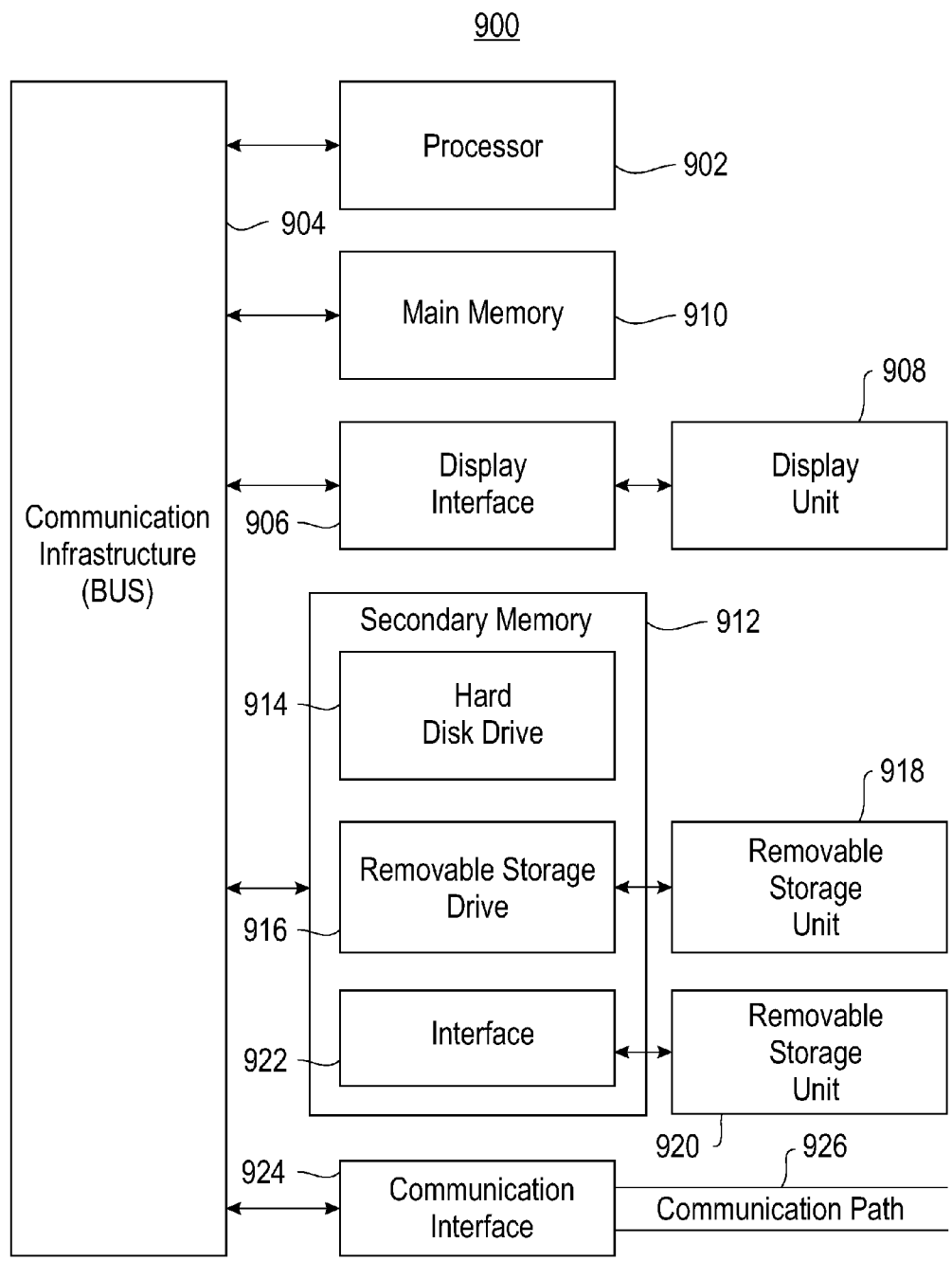
FIG. 9 is a block diagram showing system for implementing an embodiment of the present invention.

Referring now to FIG. 9 is a block diagram showing system for implementing an embodiment of the present invention. The computer system includes one or more processors, such as a processor (902). The processor (902) is connected to a communication infrastructure (904) (e.g., a communications bus, cross-over bar, or network). The computer system can include a display interface (906) that forwards graphics, text, and other data from the communication infrastructure (904) (or from a frame buffer not shown) for display on a display unit (908). The computer system also includes a main memory (910), preferably random access memory (RAM), and may also include a secondary memory (912). The secondary memory (912) may include, for example, a hard disk drive (914) and/or a removable storage drive (916), representing, for example, a floppy disk drive, a magnetic tape drive, or an optical disk drive. The removable storage drive (916) reads from and/or writes to a removable storage unit (918) in a manner well known to those having ordinary skill in the art. Removable storage unit (918) represents, for example, a floppy disk, a compact disc, a magnetic tape, or an optical disk, etc., which is read by and written to by removable storage drive (916). As will be appreciated, the removable storage unit (918) includes a computer readable medium having stored therein computer software and/or data.

In alternative embodiments, the secondary memory (912) may include other similar means for allowing computer programs or other instructions to be loaded into the computer system. Such means may include, for example, a removable storage unit (920) and an interface (922). Examples of such means may include a program package and package interface (such as that found in video game devices), a removable memory chip (such as an EPROM, or PROM) and associated socket, and other removable storage units (920) and interfaces (922) which allow software and data to be transferred from the removable storage unit (920) to the computer system.

The computer system may also include a communications interface (924). Communications interface (924) allows software and data to be transferred between the computer system and external devices. Examples of communications interface (924) may include a modem, a network interface (such as an Ethernet card), a communications port, or a PCMCIA slot and card, etc. Software and data transferred via communications interface (924) are in the form of signals which may be, for example, electronic, electromagnetic, optical, or other signals capable of being received by communications interface (924). These signals are provided to communications interface (924) via a communications path (i.e., channel) (926). This communications path (926) carries signals and may be implemented using wire or cable, fiber optics, a phone line, a cellular phone link, a radio frequency (RF) link, and/or other communication channels.

In this document, the terms "computer program medium," "computer usable medium," and "computer readable medium" are used to generally refer to media such as main memory (910) and secondary memory (912), removable storage drive (916), and a hard disk installed in hard disk drive (914). Computer programs (also called computer control logic) are stored in main memory (910) and/or secondary memory (912). Computer programs may also be received via a communication interface (924). Such computer programs, when run, enable the computer system to perform the features of the present invention as discussed herein. In particular, the computer programs, when run, enable the processor (902) to perform the features of the computer system. Accordingly, such computer programs represent controllers of the computer system.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

ALTERNATIVE EMBODIMENT

It will be appreciated that, although specific embodiments of the invention have been described herein for purposes of illustration, various modifications may be made without departing from the spirit and scope of the invention. In particular, the system and process can be employed for various cardiac disease identification and decision support. More specifically, the technique(s) described above are employed to retrieve similar case data and hence similar patients, to enable enhanced decision making for physicians. For example, using similar case data, physicians can validate their current hypothesis. By examining the associated diseases with the similar patient cases retrieved, physicians can check for any overlooked possibilities or alternate interpretations. The physicians can learn of statistical correlations or co-morbidities between diseases, treatment and outcomes, thus paving the way for a whole new way of practicing medicine. While structured clinical information such as demographics, and vital signs is clearly relevant, the most challenging aspect of finding similar cases is determining similarity in unstructured modality data. What makes two X-ray images, or two echocardiogram videos similar is not their color or texture but the underlying disease they depict. Accordingly, the scope of protection of this invention is limited only by the following claims and their equivalents.

We claim:

1. A method comprising:
storing in a database at least one continuous wave (CW) Doppler image and at least one characteristic associated with each of the at least one stored Doppler image in a form of an envelope curve;
gathering, by a processor, a query Doppler image, and extracting the envelope curve from a velocity profile associated with a query image;
matching, by the processor, the at least one characteristic associated with said at least one stored image with at least one characteristic associated with the envelope curve extracted from the query image; and
retrieving, by the processor, from the database at least one image having characteristics matching the characteristics associated with the query image.

2. The method of claim 1, further comprising:
extracting said (CW) Doppler image from an echo-cardiogram video; and
isolating the velocity profile from said extracted Doppler image.

3. The method of claim 1, further comprising determining a heart beat cycle within said envelope curve of the query image and normalizing the envelope curve to include at least one heart beat cycle and a fixed image size.

4. The method of claim 3, further comprising each characteristic associated with the envelope curve reflecting a shape of the envelope curve, wherein matching characteristics associated with a stored image and the characteristics associated with the query image is based upon a shape similarity of the envelope curve of the query image and an envelope curve of the stored image.

5. The method of claim 1, further comprising determining a shape similarity of the envelope curve of the at least one stored image with the query image by selecting a non-rigid time transform to minimize a difference between the shapes of the envelope curve of the query image and the envelope curve of the at least one stored image.

6. The method of claim 5, further comprising representing said at least one characteristic associated with said envelope curves of the query and stored images through fiducial points, said fiducial points chosen as corners in a line segment approximation for each envelope curve.

7. A system comprising:
a database to store at least one continuous wave (CW) Doppler image and at least one characteristic associated with each of the at least one stored Doppler image in a form of an envelope curve;
a query manager to gather a query Doppler image and to extract the envelope curve from a velocity profile associated with the query image;
an image manager to match the at least one characteristic associated with the stored image with at least one characteristic associated with the envelope curve extracted by the query manager from the query image; and
a retrieval manager in communication with the image manager, the retrieval manager to retrieve from the database at least one image having a characteristic matching the characteristic associated with the query image.

8. The system of claim 7, further comprising:
the query manager to extract said Doppler image from an echo-cardiogram video; and
the query manager to isolate the velocity profile from said extracted Doppler image.

9. The system of claim 7, further comprising the query manager to determine a heart beat cycle within said envelope curve of the query image and to normalize the envelope curve to include at least one heart beat cycle and a fixed image size.

10. The system of claim 7, further comprising each characteristic associated with the envelope curve to reflect a shape of the envelope curve, wherein the image manager match of the characteristic associated with a stored image and the characteristic associated with the query image is based upon a shape similarity of the envelope curve of the query image and an envelope curve of the at least one stored image.

11. The system of claim 7, further comprising the image manager to determine a shape similarity of the envelope curve of the stored image with the query image by selection of a non rigid transform to minimize a difference between the shapes of the envelope curve of the query image and the envelope curve of the stored image.

12. The system of claim 11, further comprising the image manager to represent said at least one characteristic associated with said envelope curves of the query and stored images through fiducial points, said fiducial points chosen as corners in a line segment approximation for each envelope curve.

13. An article comprising:
a non-transitory computer readable data storage media, said media including instructions comprising:
instructions for storing in a database at least one continuous wave (CW) Doppler image and at least one characteristic associated with each of the at least one stored Doppler image in a form of an envelope curve;
instructions for gathering, by a processor, a query Doppler image, and extracting the envelope curve from a velocity profile associated with the query image;
instructions for matching, by the processor, the at least one characteristic associated with the stored image with at least one characteristic associated with the envelope curve extracted from the query image; and
instructions for retrieving, by the processor, from the database at least one image having characteristics matching the characteristic associated with the query image.

14. The article of claim 13, further comprising:
instructions for extracting said Doppler image from an echo-cardiogram video; and
instructions for isolating the velocity profile from said extracted Doppler image.

15. The article of claim 13, further comprising instructions for determining a heart beat cycle within said envelope curve of the query image and normalizing the envelope curve to include at least one heart beat cycle and a fixed image size.

16. The article of claim 13, further comprising each characteristic associated with the envelope curve reflecting a shape of the envelope curve, wherein matching the at least one characteristic associated with a stored image and the at least one characteristics associated with the query image is based upon a shape similarity of the envelope curve of the query image and an envelope curve of the at least one stored image.

17. The article of claim 13, further comprising instructions for determining a shape similarity of the envelope curve of the stored image with the query image by selecting a non rigid transform to minimize a difference between the shapes of the envelope curve of the query image and the envelope curve of the stored image.

18. The article of claim 17, further comprising instructions for representing said at least one characteristic associated with said envelope curves of the query and stored images through fiducial points, said fiducial points chosen as corners in a line segment approximation for each envelope curve.

* * * * *